(12) United States Patent
Andersson

(10) Patent No.: US 7,819,953 B2
(45) Date of Patent: Oct. 26, 2010

(54) AIR TRAP

(75) Inventor: Urban Andersson, Alvkarleby (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 496 days.

(21) Appl. No.: 11/814,679

(22) PCT Filed: Feb. 2, 2006

(86) PCT No.: PCT/SE2006/000148

§ 371 (c)(1),
(2), (4) Date: Sep. 12, 2007

(87) PCT Pub. No.: WO2006/083220

PCT Pub. Date: Aug. 10, 2006

(65) Prior Publication Data

US 2008/0134766 A1    Jun. 12, 2008

(30) Foreign Application Priority Data

Feb. 4, 2005    (SE)    .................................... 0500321

(51) Int. Cl.
*B01D 19/00* (2006.01)
(52) U.S. Cl. .......................................... 95/261; 96/210

(58) Field of Classification Search ................... 95/261; 96/210
See application file for complete search history.

(56) References Cited

U.S. PATENT DOCUMENTS

| | | | |
|---|---|---|---|
| 3,359,708 A * | 12/1967 | Barber | ........................ 96/167 |
| 3,771,288 A | 11/1973 | Wisman et al. | |
| 5,112,492 A * | 5/1992 | Ransohoff | .................. 210/656 |
| 5,203,891 A | 4/1993 | Lema | |

* cited by examiner

*Primary Examiner*—Duane Smith
*Assistant Examiner*—Douglas J Theisen
(74) *Attorney, Agent, or Firm*—Yonggang Ji

(57) ABSTRACT

The invention relates to air traps 13, particularly for chromatography systems, chromatography systems using such air traps and methods of using such chromatography systems, in which the air trap comprises a liquid inlet pipe 33, a liquid outlet pipe 35, a substantially cylindrical reservoir 25 between the inlet and outlet pipes 33, 35, and an air outlet opening, the air outlet opening being openable and closable by means of a valve, wherein the liquid inlet and outlet pipes 33, 35 connect to the reservoir 25 substantially tangentially to the reservoir wall 27, the inlet pipe 33 at a distance above the outlet pipe 35, arranged such that during use incoming liquid at a the maximum permitted flow rate travels a spiral path from the inlet pipe 33 to the outlet pipe 35.

6 Claims, 4 Drawing Sheets

Fig. 3
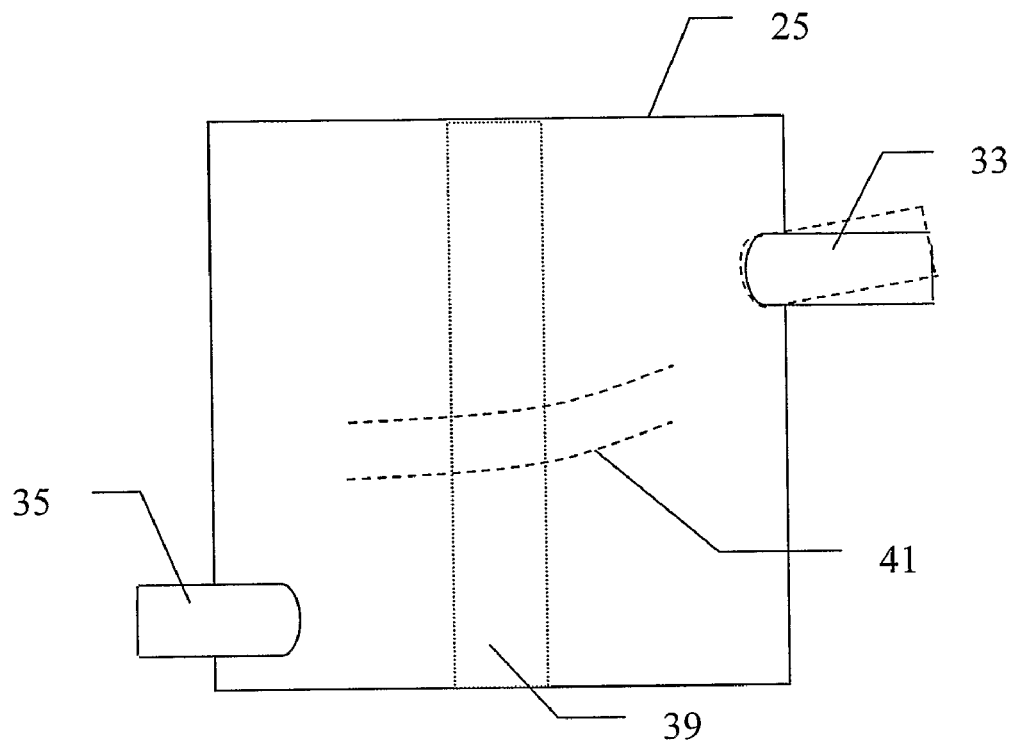
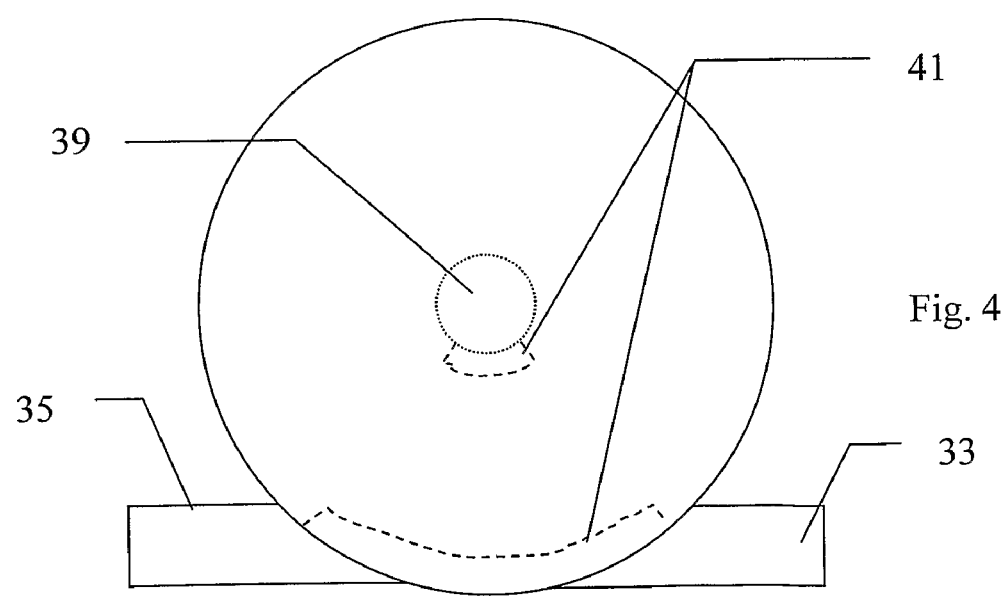
Fig. 4

AIR TRAP

CROSS-REFERENCE TO RELATED APPLICATIONS

This application is a filing under 35 U.S.C. §371 and claims priority to international patent application number PCT/SE2006/000148 filed Feb. 2, 2006, published on Aug. 10, 2006, as WO 2006/083220, which claims priority to patent application number 0500321-5 filed in Sweden on Feb. 4, 2005; the disclosures of which are incorporated herein by reference in their entireties.

FIELD OF THE INVENTION

The present invention relates to air traps for removing gas bubbles from liquids, chromatographic systems provided with such air traps and methods for removing gas bubbles from chromatographic systems.

BACKGROUND OF THE INVENTION

The present invention is directed to air traps, and is particularly concerned with an arrangement for trapping and removing air or other gas bubbles from a liquid chromatography system.

In liquid chromatography a liquid sample is passed by a flowing stream of liquid solvent (the mobile phase) through a column packed with particulate matter (stationary phase). While passing through the column the various components in the sample separate from one another by adsorbing and desorbing from the stationary phase at different rates such that these individual components elute from the column at different times. The separated components then flow through a detector which responds to each component both qualitatively and quantitatively thereby providing information to the user about the separation achieved by the chromatography column.

The particulate matter in the chromatography column is generally referred to as the chromatography media and the resolution of a separation of the stream into individual components by the chromatography media is a primary measure determinant of the economic value of the chromatography.

Accordingly it is necessary to protect the chromatography media from conditions which will ruin the media including the presence of air and the presence of microbial contamination.

The presence of air (or other gas—in the following, in the interests of brevity, "air" and "gas" are used interchangeably to mean air and/or any other gas) in a chromatography column fills the pores of the chromatography media and blocks the liquid sample from getting to the active sites of the media. Additionally the presence of air disrupts the flow of the liquid sample which makes it impossible to achieve an even flow of the liquid sample through the column Additionally, dissolved air in the liquid may form bubbles under conditions of reduced pressure which are often present after the outlet of a chromatography column and these bubbles can interfere with the performance of detectors used to register the presence or absence of components of interest in the liquid leaving the column.

Microbial or bacterial contamination is a particular problem with low pressure chromatography because the liquid phase is aqueous and the gel media a carbohydrate. The presence of air can allow bacteria to grow which interferes with the ability of the media to produce a clean, pure product.

Accordingly it is highly desirable to prevent air from entering the column and to provide a air trap that not only excludes air from entering the column but also is of a sanitary design which inhibits the growth of bacteria within the chromatography system and, in particular the chromatography column Air traps are a known technique in liquid chromatography for protecting the chromatography column and more specifically the chromatography media. A typical air trap comprises a reservoir located at the down stream end of a system pump for delivering a liquid to a chromatography column The reservoir supplies the liquid to the chromatography column Any air whether from air entrapped in the liquid, or resulting from a slow leak or from a dry line condition would be trapped in the upper portion of the reservoir above the level of the liquid therein.

An example of such an air trap is known from U.S. Pat. No. 5,112,492. This teaches that the air trap may be positioned in a liquid chromatography system at the down stream end of the system pump and upstream of the chromatography column The air trap functions as a reservoir for receiving the entire volume output of the system pump and is provided with an inlet and an outlet (each provided with a valve) in the base of the reservoir and a top exhaust valve. The inlet and outlet valves are normally opened during operation while the exhaust valve is normally closed. A bypass valve may be located between the inlet and outlet valves to the air trap so that the air trap can be bypassed for certain operations such as sample loading of the liquid column The reservoir includes level detection devices at spaced elevations in the reservoir for the purpose of maintaining the liquid level above the outlet.

The operation of the air trap is controlled by a controller which receives inputs from the level sensors and sets the valves on the automated air trap according to the controller design. During normal operation, the air trap controls the level of the liquid between the lower and upper sensing levels and will shut down the operation in the event the liquid level can not be maintained between these two elevations.

During normal operation, the air trap will have inlet and outlet valves open. If the liquid level falls below the lower elevation, the system infers that air is being detected at the lower elevation, the outlet valve will close and the exhaust valve will open until the liquid level rises and it is detected at the upper elevation. If upper level detection of liquid does not occur within a preset time period, which will be dependent on the refill flow rate and on the air trap volume, then the system will shut down because a dry inlet line condition is inferred and the condition must be corrected before continuing operation.

In order to avoid bubbles in the incoming liquid being drawn into the outlet of the reservoir it is necessary to provide a distance between the inlet and outlets which is sufficiently long enough to allow incoming bubbles to rise to the top of the reservoir before the volume of liquid that they were present in leaves the reservoir. This requires a large reservoir volume which leads to an undesirable delay in the time it takes the sample being supplied to the chromatography column to reach the column.

BRIEF DESCRIPTION OF THE INVENTION

According to the present invention, at least some of the problems with the prior art are solved by means of an air trap system having the features present in the characterising part of claim 1, a chromatography system in accordance with claim 5 and a method in accordance with claim 6.

BRIEF DESCRIPTION OF THE FIGURES

FIG. 3 shows a lateral view of the air trap of FIG. 2 and, in dashed lines, further embodiments of air traps in accordance with the present invention.

FIG. 4 shows a plan view of the air trap of FIG. 2.

DETAILED DESCRIPTION OF THE INVENTION

Figure 1:
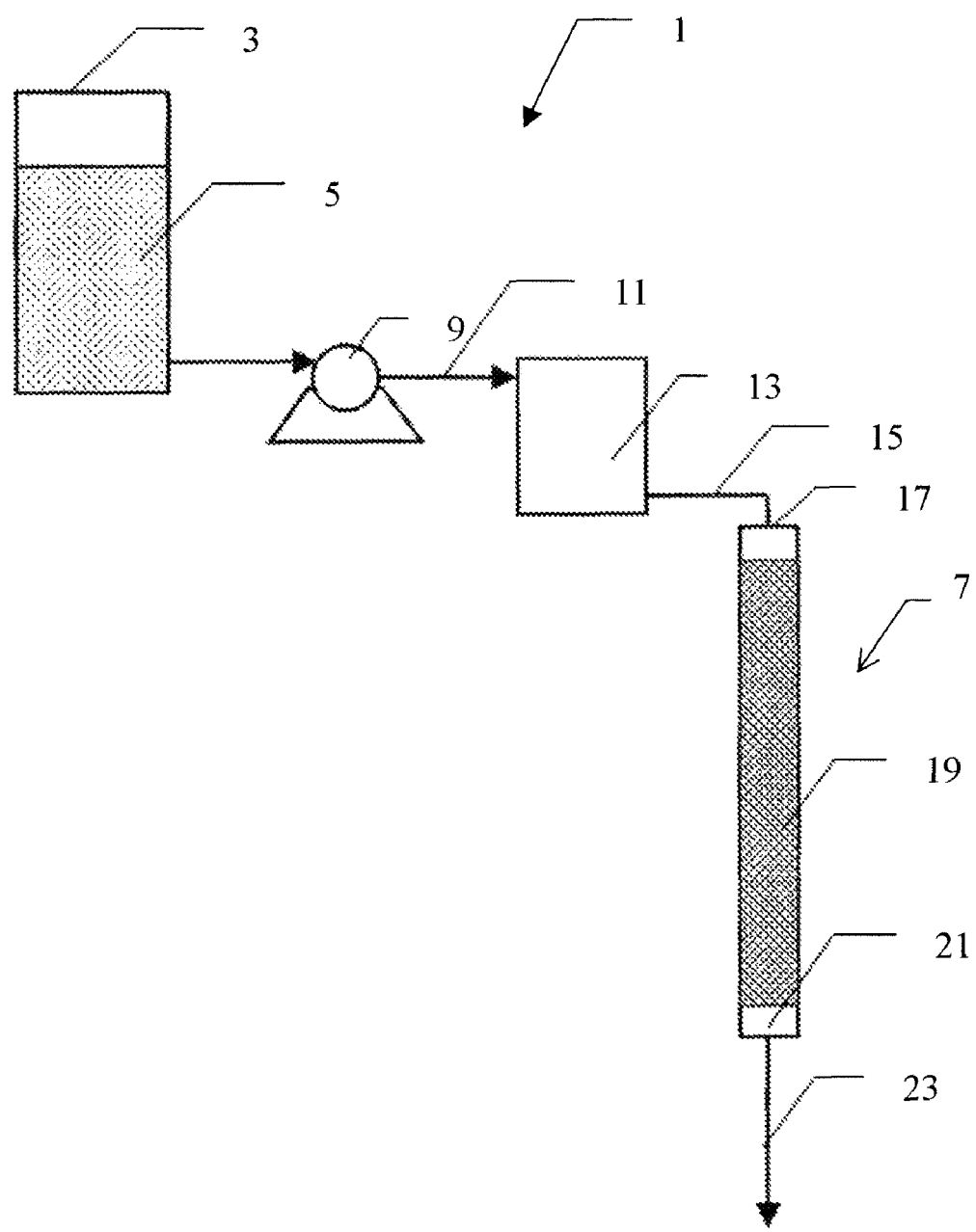
FIG. 1 shows schematically a first embodiment of a chromatography system in accordance with the present invention.

An example of a chromatographic system in accordance with the present invention is shown schematically in FIG. 1. Features of such systems which are well-known in the art and which are not relevant to present invention have been omitted for clarity of illustration. The system 1 comprises a source 3 of liquid 5 which is to be passed through at least one chromatography column 7. The liquid is pumped by a pump 9 though a conduit 11 to an air trap 13 in accordance with the present invention before continuing through conduit 15 to the inlet 17 of chromatography column 7. The liquid passes through media 19 in the column and exits the column via the outlet 21 of the column 7 into conduit 23. Conduit 23 leads the liquid to a further destination which could be, for example, a further column, a storage tank, a fraction collector or a waste drain.

Figure 2:
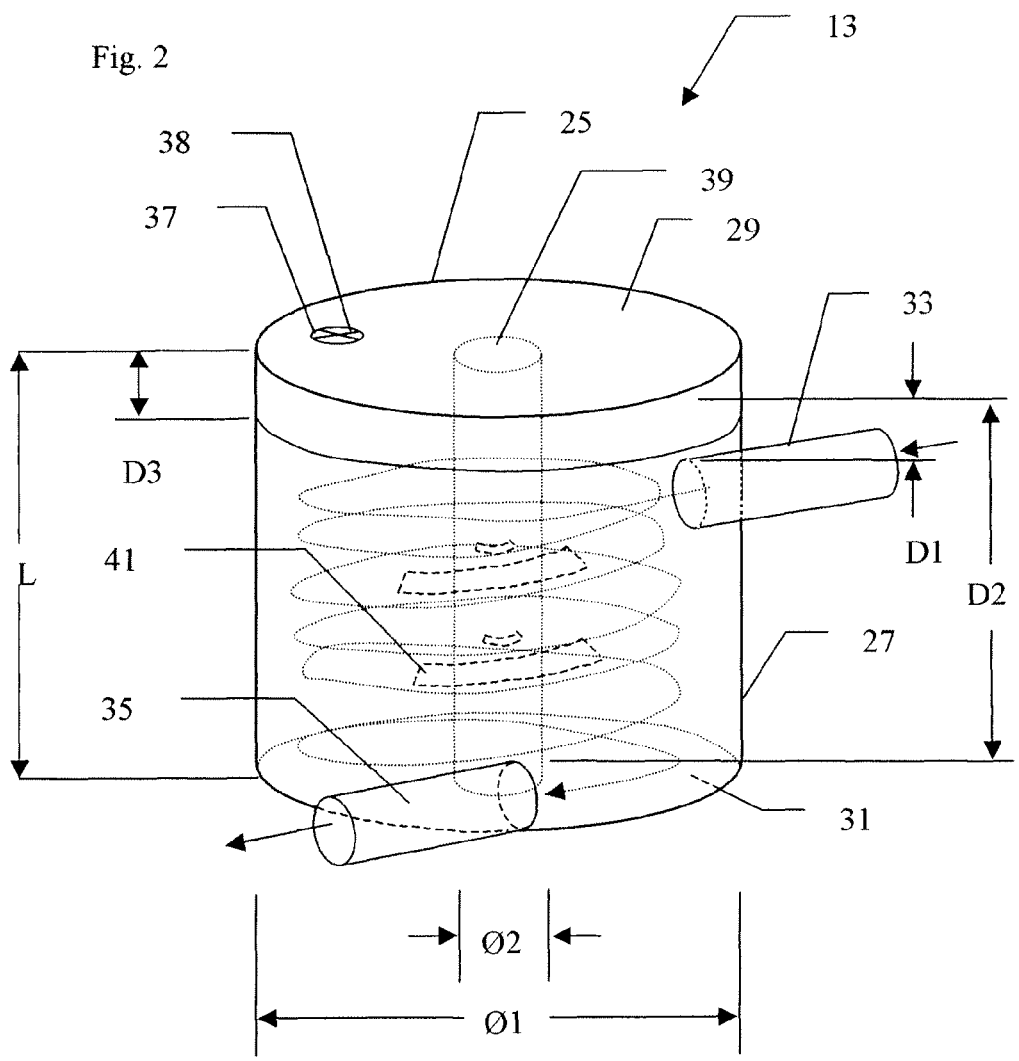
FIG. 2 shows schematically a perspective view of a first embodiment of an air trap in accordance with the present invention.

FIG. 2 shows a perspective view of one embodiment of an air trap 13 in accordance with the present invention. FIGS. 3 and 4 show respectively a lateral and a plan view of the same air trap 13. Air trap 13 comprises an air tight cylindrical reservoir 25 with a cylindrical wall 27 of length L and diameter Ø1, capped at one end by a first end surface 29 and at the other end by second end surface 31. In this example the reservoir 25 is shown orientated with its longitudinal axis substantially vertical and end surface 29 on top. Optionally, reservoir 25 may be made of a transparent material or be provided with transparent windows to allow visual inspection of the interior of the reservoir 25.

Reservoir 25 is provided with an inlet pipe 33 which is attached to and penetrates the wall 27 with its closest approach to first end surface 29 being at a distance D1 from the first end surface 29. Inlet pipe 33 is arranged to penetrate wall 27 at a tangent to wall 27. Reservoir 25 is further provided with an outlet pipe 35 which is attached to, and penetrates the wall 27, with its closest approach to first end surface 29 being at a distance D2 which is greater than D1 from the first end surface 29. Outlet pipe 35 is arranged to penetrate wall 27 at a tangent to wall 27 and may optionally, to facilitate maintenance access to the inlet and outlet pipes 33, 35, be arranged so that when looking down from the first end surface 29 towards second end surface 31, it appears that inlet pipe 33 is substantially aligned with outlet pipe 35. Upper end surface 29 is provided with an air outlet opening 37 and exhaust valve 38 which is able to be manually and/or automatically operated to release gas trapped inside the air trap.

A level sensor is arranged to detect when the level of liquid in the reservoir 25 falls to a level D3 where D3 is less than D1. If the occurs then exhaust valve 37 may be operated to release gas from the reservoir and allow the level of liquid to rise in order to avoid disturbances in the flow path. This arrangement ensures that there is always a minimum depth of liquid in the reservoir 25 during use. Optionally, and preferably, reservoir 25 is provided with a central protuberance 39 which has a diameter Ø2 which is less than Ø1. Central protuberance 39 may extend from the second end surface 31 to the first end surface 29 as shown in FIG. 2, or, in another embodiment of the present invention (see FIG. 5), from the second end surface to a distance D4 which is less than the full height of the reservoir. Central protuberance 39 serves to limit the lowest attainable velocity in the centre of the reservoir and reduces the tendency for stagnant volumes to form in the reservoir 25. At the same time, the volume liquid contained in the reservoir 25 is reduced.

In use, the pumped liquid enters reservoir 25 through inlet pipe 33 at the upper side of the reservoir 25, somewhat below the liquid surface in the reservoir 25. The path that incoming liquid takes between the inlet and outlet pipes 33, 35 depends on its flow rate. At a low flow rate which depends, amongst others, on the viscosity of the liquid, the positioning of the inlet and outlet pipes and the distance between them, the incoming fluid takes the shortest path between the inlet and outlet pipes and is subjected to little or no centrifugal force. In this case bubbles leave the liquid by rising under the influence of gravity. As the flow rate of the incoming liquid increases its tangential velocity component is too high for it to take the shortest path between the inlet and outlet pipes. Instead, the liquid is forced to circulate around the curved wall of the reservoir 25, and is subject to centrifugal forces. The liquid is forced by its tangential velocity component, the shape of the reservoir 25 and the positioning of the inlet and outlet pipes 33, 35 to follow a spiral path downwards and finally out of the reservoir 25 via outlet pipe 35.

Since the centrifugal forces acts more strongly on the liquid (which has a higher density than air), air is pressed toward the centre of the reservoir 25 (where the velocity is lower) while at the same time it floats upwards due to the effect of the force of gravity. As the outlet is on the circumference of the reservoir and bat a lower level than the inlet the combined influence of gravitational and centrifugal forces provide a more efficient de-airing and enables an air trap according to the present invention to have a lower liquid volume that prior art air traps of similar de-airing capacity used in chromatography systems.

Optionally, as shown in FIGS. 2-4, vanes 41 may be provided inside the reservoir 25 to guide the liquid in a spiral path from the inlet pipe 33 to the outlet pipe 35.

As shown by dashed lines in FIG. 3, in another embodiment of the present invention the inlet pipe 33 is arranged to be not parallel with the end surfaces of the reservoir, instead it is inclined towards the second end surface, so that incoming liquid is inputted with a flow vector in a direction towards the second end surface 31.

Figure 5:
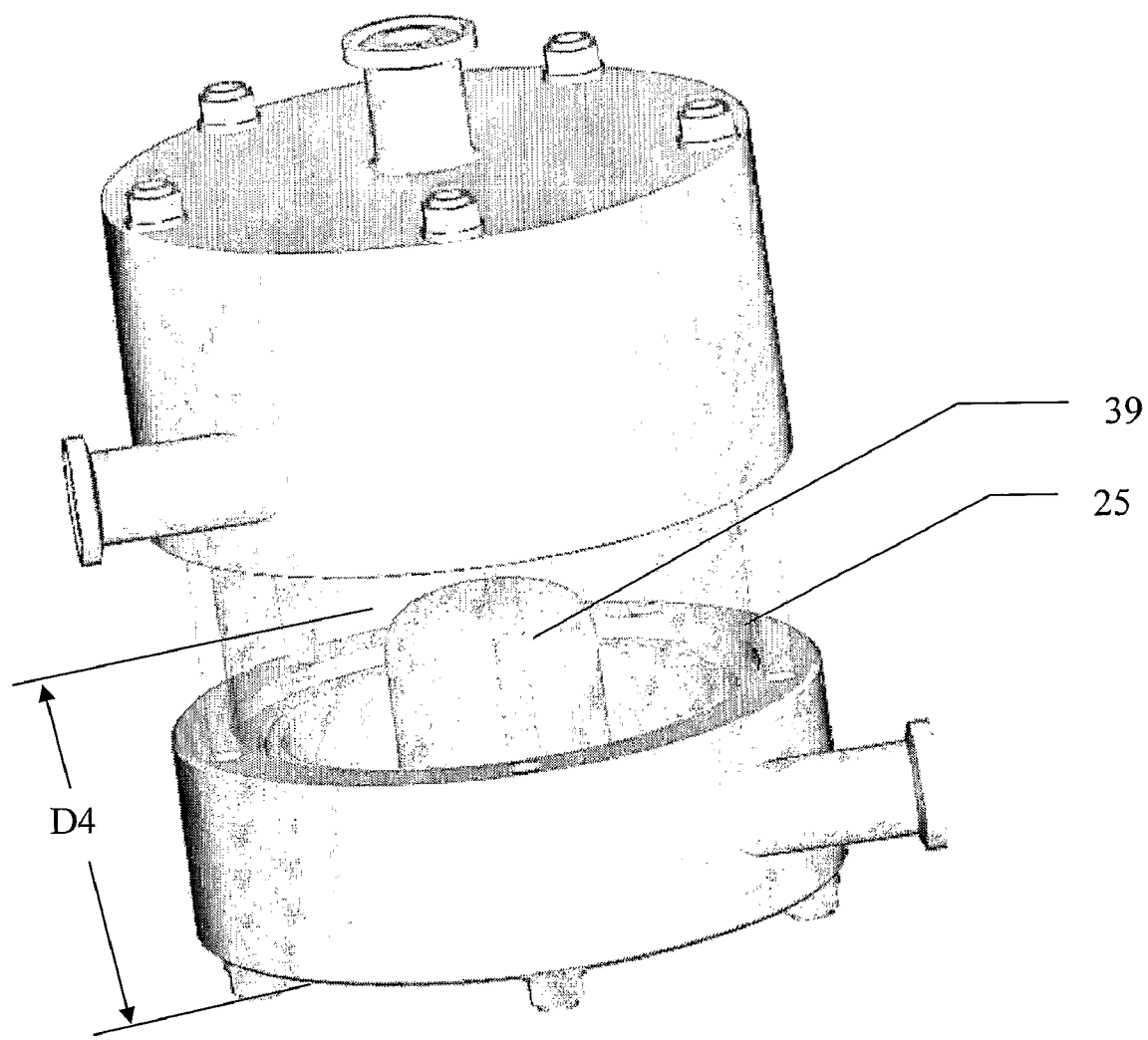
FIG. 5 shows a perspective view of an embodiment of an air trap in accordance with the present invention.

FIG. 5 shows a perspective view of an embodiment of an air trap in accordance with the present invention in which the reservoir has a transparent wall and the central protuberance.

An air trap in accordance with the present invention has the advantage that the separation of bubbles from liquid increases as the flow velocity through the air trap increases, in other words the faster the flow, the better the separation. This is in contrast to prior art air traps used in chromatography systems which have had an inverse relationship between flow velocity and separation. Additionally, even at liquid flows rates too low to cause the incoming liquid to take a spiral path from the inlet to the outlet of the reservoir an adequate remove of air bubbles from the incoming liquid can be achieved. This is because with such flow rates the liquid takes a relatively long time to travel from the upper inlet pipe to the lower outlet pipe and this allows bubbles in the liquid enough time to rise to the top of the reservoir.

Preferably an air trap in accordance with the present invention is designed such that when it is operated at its maximum permitted flow rate the centrifugal force exerted on the fluid flowing along a spiral path through the reservoir is at least 1 G. More preferably the centrifugal force exerted on the fluid when flowing along a spiral path through the reservoir at the maximum permitted flow rate is at least 2 G. Even more preferably the centrifugal force exerted on the fluid when flowing along a spiral path through the reservoir at the maximum permitted flow rate is at least 3 G. The dimensions of an air trap needed to give the abovementioned forces can be calculated from the following:

The centrifugal acceleration ($a_{cent}$) that drives the separation depends on the tangential velocity component ($v_t$) and the radius of the air trap ($R_{trap}$). Since $v_t$ is proportional to the flow rate at the inlet to the air trap, an expression for the $a_{cent}$ is obtained:

$$a_{cent} = \frac{v_t^2}{R_{trap}} \propto \left(\frac{Q}{A_{inlet}}\right)^2 / R_{trap}$$

where

Q is the volume flow through the air trap, and $A_{inlet}$ is the area of the cross sectional area of the air trap inlet.

In order to provide a centrifugal acceleration that gives a better air separating effect than that obtained by the gravitational acceleration (G), i.e. the separating centrifugal effect dominates the gravitational separating effect, an important design criteria is to determine a minimum value for the ratio between $a_{cent}$ and G, for example:

$$\frac{a_{centMAX}}{G} \propto \left(\frac{Q_{MAX}}{A_{inlet}}\right)^2 / (gR_{trap}) \geq 2$$

ie., based on a maximum permitted flow rate ($Q_{MAX}$) through the trap, and the assumption that the centrifugal acceleration ($a_{cent}$) should be at least equal to the gravitational acceleration (G), the radius of the air trap ($R_{trap}$) can be determined for a specific inlet area. Typically the inlet area is the same as the general conduit diameter of the separation system in which the air trap is installed but this is not obligatory.

The skilled person will recognise that other orientations of the air trap in accordance with the present invention are also possible, for example with the longitudinal axis of the reservoir inclined at an angle, provided arrangements are made to ensure correct functioning of the exhaust valve, level sensing and, preferably, that drainage of all to liquid from the trap can be readily achieved.

The above examples illustrate specific aspects of the present invention and are not intended to limit the scope thereof in any respect and should not be so construed. Those skilled in the art having the benefit of the teachings of the present invention as set forth above, can effect numerous modifications thereto. These modifications are to be construed as being encompassed within the scope of the present invention as set forth in the appended claims.

What is claimed is:

1. An air trap for removing air in a liquid flowing through a chromatography system, wherein the air trap comprises a liquid inlet pipe (33), a liquid outlet pipe (35), a substantially cylindrical reservoir (25) between the inlet and outlet pipes, and an air outlet opening (37), the air outlet opening being openable and closable by means of a valve (38), wherein the liquid inlet and outlet pipes (33, 35) connect to the reservoir (25) substantially tangentially to the reservoir wall (27), the inlet pipe (33) at a distance above the outlet pipe (35), arranged such that during use incoming liquid at a flow rate equal to its maximum permitted flow rate travels a spiral path from the inlet pipe (33) to the outlet pipe (35), wherein said air trap is a sanitary design.

2. The air trap of claim 1, wherein a substantially cylindrical protuberance (39) protrudes axially from the bottom of the reservoir (25).

3. The air trap of claim 1, wherein it is designed such that during use incoming liquid at a flow rate equal to its maximum permitted flow rate travels a spiral path from the inlet pipe (33) to the outlet pipe (35) and is subject to centrifugal force of at least 1 G.

4. The air trap of claim 1, wherein it is designed such that during use incoming liquid at a flow rate equal to its maximum permitted flow rate travels a spiral path from the inlet pipe (33) to the outlet pipe (35) and is subject to centrifugal force of at least 2 G.

5. A chromatography system comprising a source of liquid, a pump for pumping said liquid from said source via the air trap of claim 1 to a chromatography column.

6. A method for removing air in a liquid flowing through a chromatography system, characterised by the step of operatively providing the system with the air trap of claim 1.

* * * * *